(12) United States Patent
Marquette et al.

(10) Patent No.: US 8,735,116 B2
(45) Date of Patent: May 27, 2014

(54) HIGH-DENSITY SPOT SEEDING FOR TISSUE MODEL FORMATION

(75) Inventors: Michele L. Marquette, Texas City, TX (US); Marguerite A. Sognier, Houston, TX (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 278 days.

(21) Appl. No.: 12/880,602

(22) Filed: Sep. 13, 2010

(65) Prior Publication Data

US 2012/0064596 A1 Mar. 15, 2012

(51) Int. Cl.
| | | |
|---|---|---|
| C12N 11/00 | (2006.01) | |
| C12N 11/16 | (2006.01) | |
| C12N 5/00 | (2006.01) | |
| A61K 35/12 | (2006.01) | |
| C12N 5/071 | (2010.01) | |
| C12N 5/07 | (2010.01) | |

(52) U.S. Cl.
CPC ............. *C12N 5/00* (2013.01); *C12N 5/0062* (2013.01); *C12N 5/06* (2013.01); *C12N 5/0602* (2013.01); *C12N 5/0657* (2013.01); *C12N 5/0658* (2013.01)
USPC .............. 435/174; 435/1.1; 435/325; 435/29; 435/375; 435/377

(58) Field of Classification Search
USPC ........................................... 435/174
See application file for complete search history.

(56) References Cited

U.S. PATENT DOCUMENTS

| | | |
|---|---|---|
| 6,514,756 B1 | 2/2003 | Braun et al. |
| 6,555,377 B1 | 4/2003 | Braun et al. |
| 2003/0113301 A1 | 6/2003 | Edge et al. |
| 2003/0211130 A1 | 11/2003 | Sanders et al. |
| 2003/0212024 A1 | 11/2003 | Keating et al. |
| 2004/0082063 A1* | 4/2004 | Deshpande et al. ........ 435/366 |
| 2004/0087016 A1 | 5/2004 | Keating et al. |
| 2005/0009178 A1 | 1/2005 | Yost et al. |
| 2006/0198827 A1 | 9/2006 | Levenberg et al. |
| 2008/0193910 A1* | 8/2008 | Larkin et al. ................... 435/1.1 |
| 2008/0227738 A1 | 9/2008 | Keating et al. |
| 2009/0162436 A1* | 6/2009 | Carson et al. ................. 424/484 |

FOREIGN PATENT DOCUMENTS

| | | |
|---|---|---|
| JP | 2003259863 | 9/2003 |
| WO | WO 03/072748 | 9/2003 |

OTHER PUBLICATIONS

Liu, Y.; et al; "Optimization of a natural collagen scaffold to aid cell-matrix penetration for urologic tissue engineering" Biomaterials, 30, 3865-3873, 2009.*
Singh, Poonam; et al; "Micromass culture: a recent in vitro system for testing embryotoxic potential of chemicals" Indian Journal of Science and Technology, 2, 53-56, 2009.*
Flint, O.P.; "A Micromass Culture for Rat Embryonic Neural Cells" Journal of Cellular Science, 61, 247-262, 1983.*
Swalla, Billie J.; et al; "The Independence of Myogenesis and Chondrogenesis in Micromass Cultures of Chick Wing Buds" Developmental Biology, 116, 31-38, 1986.*
Handschel, Jorg G.K.; et al; "Prospects of micromass culture technology in tissue engineering" Head & Face Medicine, 3, 2007.*
Radisic, Milica; et al; "High-Density Seeding of Myocyte Cells for Cardiac Tissue Engineering" Biotechnology and Bioengineering, 82, 403-414, 2003.*
Facer, et al., Rotary Culture Enhances Pre-osteoblasts, J Dent Res 84(6): 545-547, 2005.
Dennis R.G., Kosnik P, Excitability and isometric contractile properties of mammalian skeletal muscle constructs engineered in vitro. In Vitro Cell. Dev. Biol. Anim. 36(5): 327-335, 2000.

* cited by examiner

*Primary Examiner* — Blaine Lankford
*Assistant Examiner* — David Berke-Schlessel
(74) *Attorney, Agent, or Firm* — Kurt G. Hammerle

(57) ABSTRACT

A method for making a tissue includes seeding cells at a selected concentration on a support to form a cell spot, incubating the cells to allow the cells to partially attach, rinsing the cells to remove any unattached cells, adding culture medium to enable the cells to proliferate at a periphery of the cell spot and to differentiate toward a center of the cell spot, and further incubating the cells to form the tissue. The cells may be C2C12 cells or other subclones of the C2 cell line, H9c2(2-1) cells, L6 cells, L8 cells, QM7 cells, Sol8 cells, G-7 cells, G-8 cells, other myoblast cells, cells from other tissues, or stem cells. The selected concentration is in a range from about $1\times10^5$ cells/ml to about $1\times10^6$ cells/ml. The tissue formed may be a skeletal muscle tissue, a cardiac muscle tissue, nerve tissue, or a bone tissue.

9 Claims, 5 Drawing Sheets

HIGH-DENSITY SPOT SEEDING FOR TISSUE MODEL FORMATION

ORIGIN OF THE INVENTION

The inventions claimed herein were made in the performance of work under a NASA contract and is subject to Public Law 96-517 (35 U.S.C. §200 et seq.). The contractor has not elected to retain title.

BACKGROUND OF INVENTION

Field of the Invention

The invention relates generally to methods for culturing cells to form tissue models, particularly models of muscle tissue,

SUMMARY OF INVENTION

One embodiment described herein relates to a method for culturing cells to form tissue comprising the steps of seeding cells at a selected concentration on a support to form a cell spot, incubating the cells to allow the cells to initially or partially attach to the support, rinsing the cells gently after initial or partial attachment to remove any cells that are unattached, adding growth medium to the support after rinsing such that the attached cells proliferate about a periphery of the cell spot, and further incubating the cells to form tissue. The cells may be myoblasts (i.e., immature muscle cells) such as C2C12 cells or other subclones of the C2 cell line, H9c2(2-1) cells, L6 cells, L8 cells, QM7 cells, Sol8 cells, G-7 cells, G-8 cells, other myoblast cells, cells from other tissues, stem cells, or de-differentiated cells. The selected concentration for the above cells is in a range from about $1\times10^5$ cells/ml to about $1\times10^6$ cells/ml. The resulting tissue may be skeletal muscle tissue, cardiac muscle tissue, nerve tissue, or bone tissue.

Another embodiment described herein relates to tissue produced by the steps of seeding cells at a selected concentration on a support to form a cell spot, incubating the cells to allow the cells to partially attach to the support, removing any cells that are unattached after this step of incubating, adding growth medium to the support after removing the unattached cells such that the cells proliferate about the periphery of the cell spot, and additional incubating of the cells to enable tissue formation. The cells may be myoblasts such as C2C12 cells or other subclones of the C2 cell line, H9c2(2-1) cells, L6 cells, L8 cells, QM7 cells, Sol8 cells, G-7 cells, G-8 cells, other myoblast cells, cells from other tissues, stem cells, or de-differentiated cells. The selected concentration for the above cells is in a range from about $1\times10^5$ cells/ml to about $1\times10^6$ cells/ml. The resulting tissue may be skeletal muscle tissue, cardiac muscle tissue, nerve tissue, or bone tissue.

Other aspects and embodiments described herein will be apparent from the following description and the appended claims, taken in conjunction with the accompanying drawings, illustrating the principles of the embodiments by way of example only.

DETAILED DESCRIPTION OF EXEMPLARY EMBODIMENTS

Figure 1:
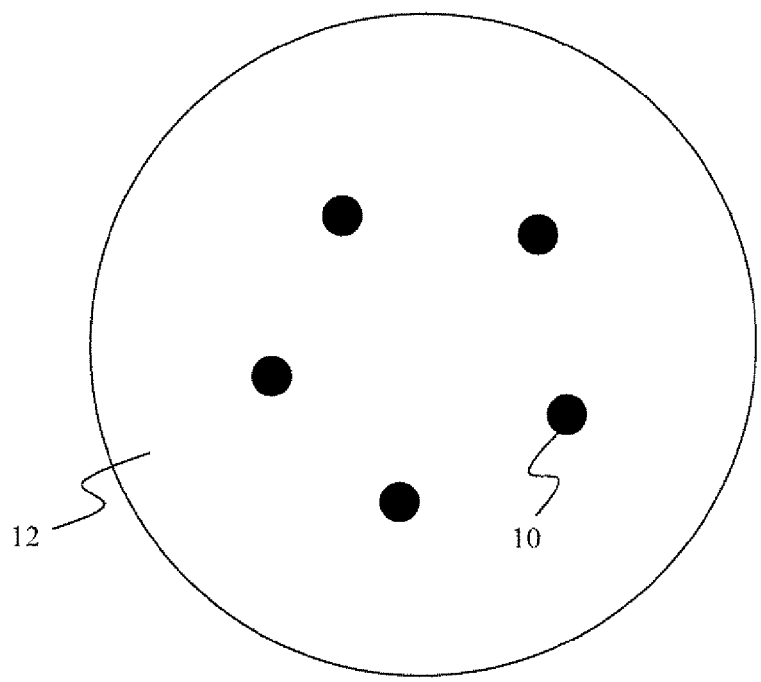
FIG. 1 shows a schematic illustrating a method of high-density spot seeding (HDSS) in accordance with embodiments described herein.

Exemplary embodiments will now be described with reference to the accompanying drawings. Like elements or components in the drawings are denoted with the same reference characters for consistency.

The exemplary embodiments described herein relate to methods for producing or forming models of tissue, such as models of muscle tissue. Such methods comprise the act of high-density seeding, which may be described as "spot seeding", of progenitor cells, followed by incubating the cells to allow the cells to proliferate, align, fuse and differentiate into mature tissues. Although the following description uses a skeletal muscle cell line as one example, one of ordinary skill in the art would appreciate that the embodiments described herein also relate to other cell types, such as nerve cells, bone cells, and cardiac muscle cells, or other anchorage-dependent cells.

For example, for skeletal muscle tissue, one can utilize any commercially available skeletal muscle progenitor cells. In accordance with one embodiment, immature muscle cells are seeded into a spot at a relatively high density. Next, the cells are incubated under conditions to allow the cells to proliferate, align, fuse, and mature into functional muscle tissue models. The skeletal muscle tissue models of the embodiments described herein may be used to study various processes involved in skeletal muscle maturation, such as proliferation, alignment, fusion (to form multinucleated cells), differentiation (production of new proteins necessary for contraction), and contraction. These models can help in the understanding of the mechanism of muscle atrophy and facilitate the development of methods or reagents to alleviate or prevent muscle atrophy. In addition, such models of muscle tissue may find use in the treatment or repair of muscle damage, such as in muscle atrophy, skeletal muscle trauma (i.e., burns), or muscle damage resulting from cardiac infarction.

In one example described herein, C2C12 cells are used, which are available from the American Type Culture Collection (ATCC) Cell Repository Line (CRL)-1772. C2C12 cells are mouse myoblastic precursor cells. Other muscle precursor cell types (myoblasts) may also be used without departing from the scope of the claims appended hereto, such as, H9c2 (2-1) cells (ATCC CRL-1446), L6 cells (ATCC CRL-1458), L8 cells (ATCC CRL-1769), QM7 cells (ATCC CRL-1962), Sol8 cells (ATCC CRL-2174), G-7 cells (ATCC CRL-1447), and 0-8 cells (ATCC CRL-1456).

Methods in accordance with embodiments described herein make use of high-density seeding of myoblasts to induce alignment, fusion, and differentiation of the cells into muscle tissue models. High-density seeding likely prevents cells from flattening in most areas of the spot of seeding except the periphery of the spot. The round cells in the center of the spot have increased cell-cell contacts, which induce expression of genes that cause the cells to switch from a proliferating phenotype to a differentiating phenotype. That is, cells originally positioned in the center of a spot are less able to further divide, due to cell contact inhibition, than cells originally positioned along the periphery of a spot, which are able to flatten and continue to proliferate As growth of cells continue from the spot of seeding, newly formed cells become spatially limited by adjacent newly formed cells and, therefore, newly formed cells are forced to align outward in a consistent manner. As more and more cells proliferate, less space is available. Cells become crowded and experience increased cell-cell contacts as they grow. As mentioned above, the increased cell-cell contacts cause the cells to switch from the proliferating phenotype to the differentiating phenotype. Thus, a timeline is established with the youngest cells (proliferating cells) at the periphery of the growing spot and the more mature cells (differentiated cells) away from the periphery and toward the center of the spot of initial seeding.

Referring now to the appended drawings, FIG. 1 illustrates a method of high-density spot seeding (HDSS) in accordance with one embodiment. Cells may be seeded as one or more "high-density" spots 10 in a culture plate 12 (with or without a coating) or other suitable support. The seeding may be performed with an appropriate "high density" for the type of cells selected, such high density normally being within a range from about $1 \times 10^5$ cells/ml to about $1 \times 10^6$ cells/ml. In an embodiment for C2C12 cells, "high density" is around $5 \times 10^5$ cells/ml, with the volume of each spot being within a range of about 20 μl to about 50 μl. More than one high-density spot may be seeded in culture plate 12 depending on the desired applications after formation of the tissue. For example, a few spots (e.g., 4-6 spots) may be introduced in a 100 mm tissue culture plate.

Figure 2:
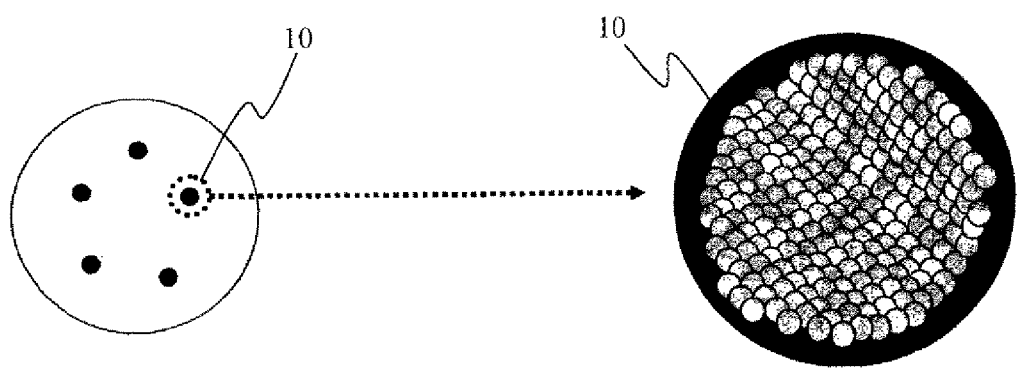
FIG. 2 shows a schematic illustrating a close-up view of a single cell spot in accordance with an embodiment described herein.

Because the concentration of the cells in a high-density spot is relatively high (as compared to the broad spectrum of density seeding techniques known to the skilled artisan), cells in each spot are in contact with each other, except for the area along the periphery of the spot. To illustrate the positioning of the plurality of cells in a "high-density" spot (although not necessarily to scale), FIG. 2 shows a close-up view of a plurality of cells clustered together in high-density spot 10 shortly after the initial step of seeding.

Figure 3:
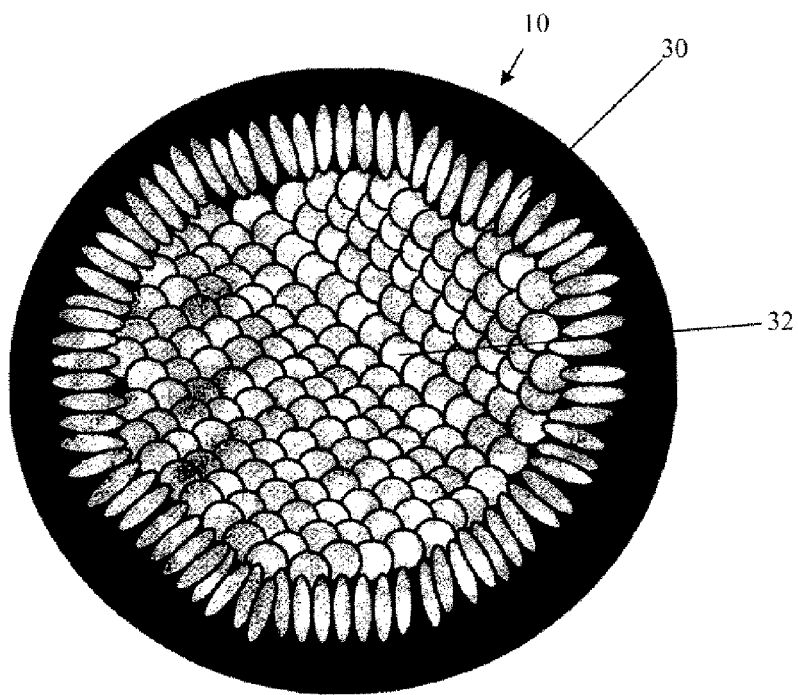
FIG. 3 shows a schematic illustrating alignment of new cells at the periphery of a single cell spot one hour after seeding in accordance with an embodiment described herein.

As noted above, cells at the periphery of spot 10 are not prevented from flattening outward. As a result, cells at the periphery will elongate outwardly after some time. FIG. 3 is a graphical representation of a close-up view of spot 10 after an initial or partial attachment period of about one hour after seeding. Cells 30 at the periphery exhibit a flattened morphology, while cells 32 in the center of spot 10 maintain a more rounded appearance. Rounded cells 32 in the center of spot 10 have more cell-cell contacts, which would induce expression of genes that cause the cells to switch from a proliferating phenotype to a differentiating phenotype. After this initial or partial attachment period, the cells at this stage are rinsed by gently adding culture medium. The act of rinsing removes loosely attached or unattached cells and eliminates them from the culture plate 12. The act of rinsing prevents cells from later dislodging from spot 10 and settling into non-spot areas. Thus, the act of rinsing helps keep large areas unobstructed by other cells, permitting the proliferating cells to grow in a direction outward from the center of spot 10 into unoccupied areas of the culture vessel and thereby align. Alignment is a functional requirement of skeletal muscle cells.

After rinsing and aspiration of the culture medium and unattached cells, additional culture (growth) medium is added to the culture plate. For a 100 mm Petri dish serving as the culture plate, the range of volume of additional culture medium added is about 10 ml to about 30 ml. The volume of culture medium at this stage of the process should be a sufficient amount of medium such that the cells may be left alone without adding more culture medium thereafter for a period of about 13 days. Further, the volume of additional culture medium should be less than what overfills the culture plate 12 so as to avoid spilling of medium during movement of the culture plate. The medium used may be the same growth or culture medium used originally during the initial step of seeding and need not be a differentiation medium that promotes cell differentiation.

Figure 4:
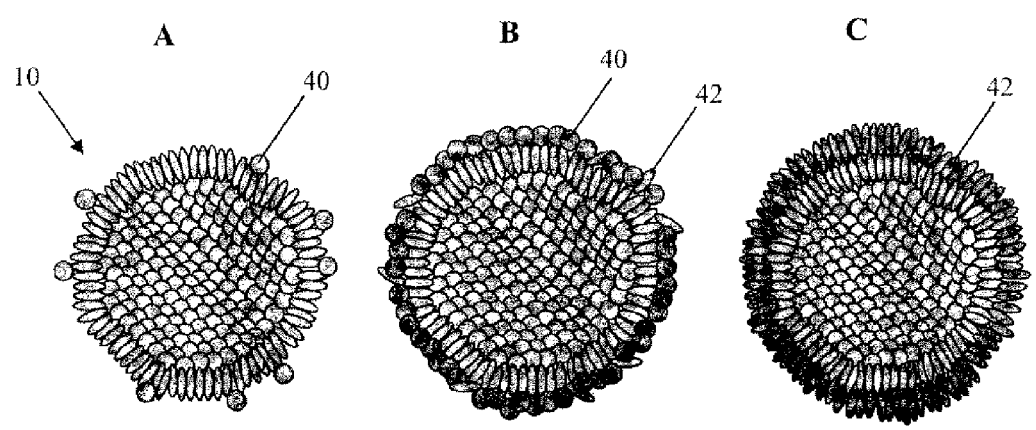
FIGS. 4A-C show schematics illustrating the progression of cell growth by proliferation and alignment of cells at the periphery of a cell spot 24-48 hours after seeding in accordance with an embodiment described herein.

Referring now to FIGS. 4A-C, a progression of the growth of the plurality of cells seeded in an exemplary spot 10 is shown as snapshots proceeding in time (from left to right) from about 24 to about 48 hours after initial seeding. As shown in FIG. 4A, new cells 40 are produced from the original cells at the periphery of spot 10. FIG. 4B shows that after more incubation, these new cells 40 begin to flatten to become flattened, proliferating cells 42. As new cells are continually produced, they eventually flatten and are forced to align in an outward direction, as shown in further progression in FIG. 4C. The continuing production, flattening, and alignment of new cells gradually increases the size of the spot.

Figure 5:
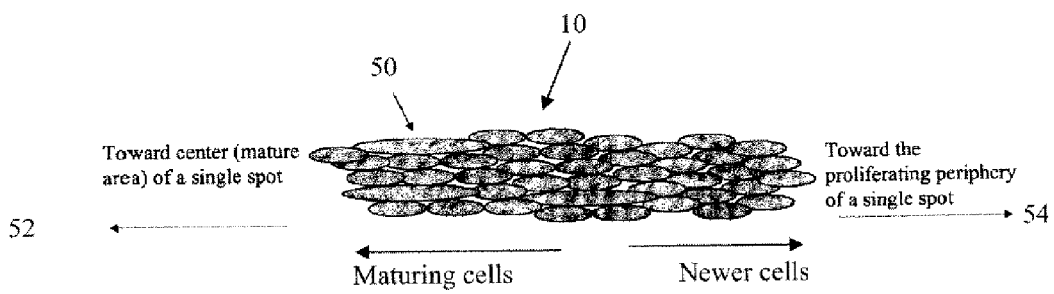
FIG. 5 shows a schematic illustrating formation of myotubes in a cell spot about 72 hours after seeding in accordance with an embodiment described herein.

FIG. 5 is a close-up illustration of a portion of the cells of an exemplary spot 10 at about 72 hours after seeding. Spontaneous differentiation of the cells can be observed at this stage without the act of switching or altering the serum. used as the growth medium. In particular, small myotubes 50, which result from fusion of the myoblasts, are observed near the center (mature area) 52. Fewer myotubes are observed towards the periphery area 54, and no myotubes are seen at the actively proliferating periphery.

Figure 6:
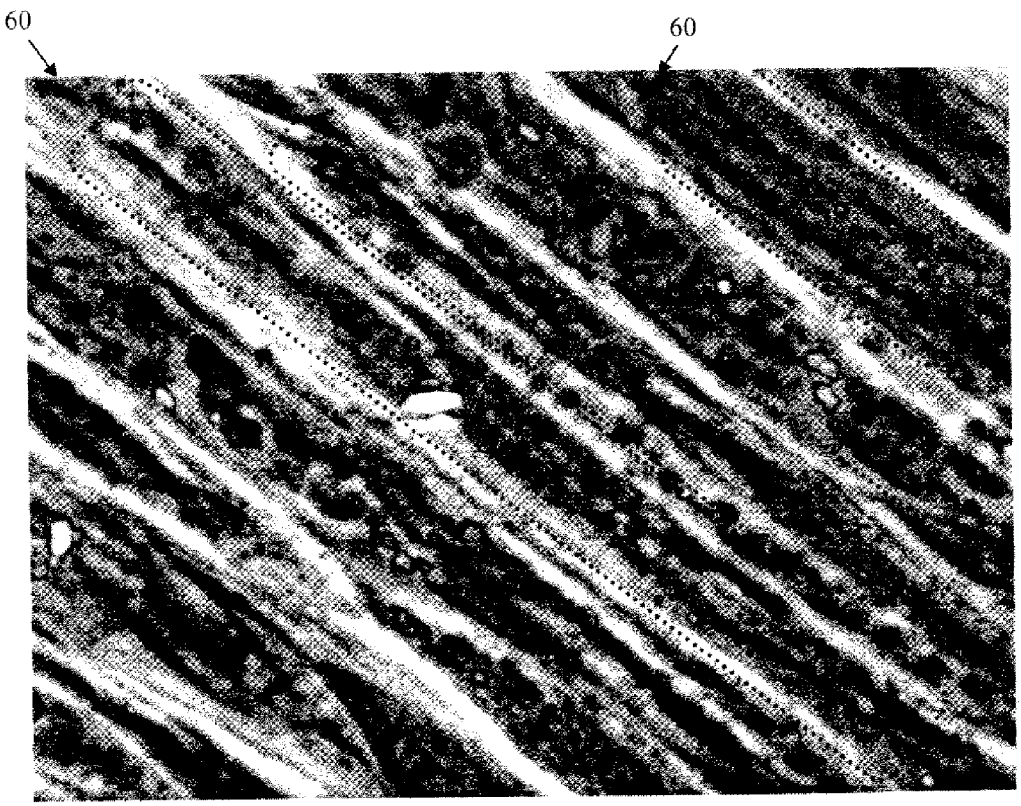
FIG. 6 shows a microscopic image of a portion of a cell spot about 8 days after seeding in accordance with an embodiment described herein.

FIG. 6 is a microscopic image of a portion of an exemplary spot 10 about 8 days after seeding. In this image, formations of multinucleated myotubes 60 are shown. The elongated multinucleated myotubes 60 are outlined by the dotted lines in the image.

Figure 7:
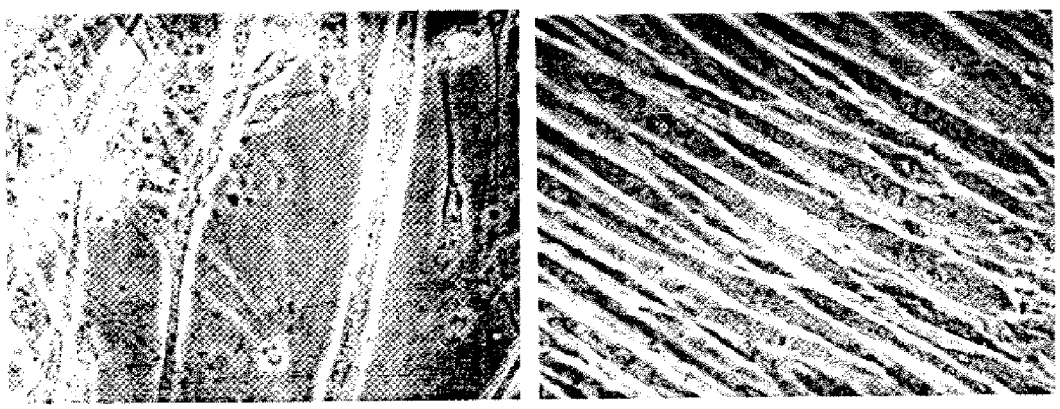
FIG. 7 shows a comparison of myotube alignments produced by serum-induced myotube culture (left panel) and by a method in accordance with an embodiment described herein (right panel).

FIG. 7 shows a comparison between myotubes produced by a method known in the related art (serum induction/deprivation) on the left panel and myotubes formed by high-density spot seeding in accordance with at least one embodiment herein described and appearing on the right panel of the drawing. Note that the myotubes on the right panel are well aligned. In contrast, the myotubes visible on the left panel, formed by the method of the related art known as serum induction/deprivation, did not generate well-aligned myotubes. The drawing suggests that myotubes produced by the method herein described mimic natural muscle tissues.

Figure 8:
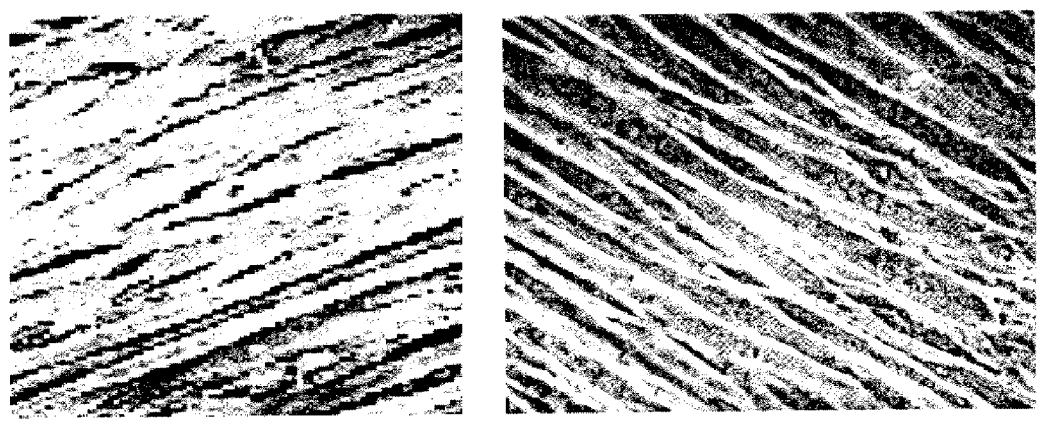
FIG. 8 shows a comparison of myotube alignments induced by using poly-(L-lactic acid) PLLA nanofiber patterning (left panel) and by a method in accordance. with an embodiment described herein (right panel).

FIG. 8 provides a comparison between myotubes shown on the left panel that are produced by another method known in the related art, using PLLA (poly L-lactic acid) nanofiber scaffolding and modified by the techniques described in the publication of Ngan Huang, et al., entitled "Myotube Assembly on Nanofibrous and Micropatterned Polymers," published in Nano Lett. 2006, Mar. 8; 6:537-542, and myotubes shown on the right panel that are produced by high-density spot seeding in accordance with embodiments described herein. Again, the myotubes formed by the method herein described are well aligned. In contrast, the alignment of myotubes formed in the presence of PLLA nanofiber scaffolding is controlled by how well the nanofibers are aligned.

Figure 9:
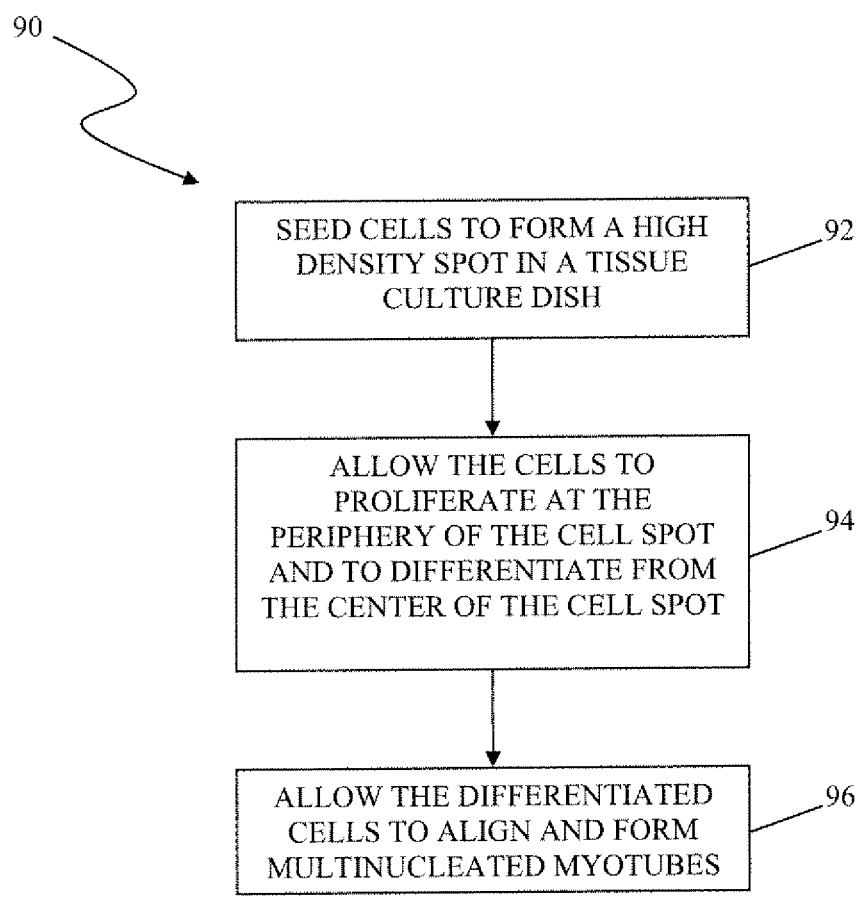
FIG. 9 is a block diagram representative of a method for forming a model of muscle tissue in accordance with an embodiment described herein.

FIG. 9 is a block diagram representative of a method for forming a model of muscle tissue in accordance with an exemplary embodiment described herein. Method 90 may start with the step of seeding a plurality of cells to form one or more high-density cell spots in a tissue culture plate or a similar support (step 92). The tissue culture plate or similar support may be modified by coating with one or more extracellular matrix components and/or one or more adhesion proteins, wherein the extracellular matrix components may be selected from the group consisting of collagens, laminins, fibronectins, elastins, keratins, heparin sulfates, chondroitin sulfates, keratin sulfates, or hyaluronic acid, and wherein the adhesion proteins may be selected from integrins or cadherins. The plurality of cells needed for seeding may be from commercial sources (e.g., ATCC) and grown in a manner known by one of ordinary skill in the art to obtain a sufficient high density before the step of spot seeding. For example, cells may be grown in culture in a flask and harvested by chemical detachment and centrifugation. Cells may be grown in an appropriate medium, such as a proliferation (i.e., growth) medium. Seeding for high density is within a range of from about $1 \times 10^5$ cells/ml to about $1 \times 10^6$ cells/ml. A cell density of about $5 \times 10^5$ cells/ml for C2C12 cells was used in the method of the Example described in more detail below.

After the cells have attached to the tissue culture dish (or other support) and the unattached cells are washed off by rinsing, additional growth medium is added such that the cells are allowed to grow in the support for an undisturbed period of time of days that are nearly two weeks long. Cells at the periphery of the spot proliferate, while cells near the center of the spot, due to contact inhibition, do not further proliferate but instead tend to differentiate into mature cells (step 94). The immature cells are allowed to align, fuse to form multinucleated myotubes, and differentiate into mature muscle tissues (step 96).

EXAMPLE

Embodiments previously described will now be illustrated with an example using a plurality of C2C12 cells to provide further details of how to form a model of muscle tissue.

First, C2C12 cells are grown or cultivated in tissue culture plates. The cells are grown using a culture or growth medium, such as Dulbecco's Modified Eagle's Medium (DMEM) and 10% fetal calf serum. The expanded cells are then detached from the culture plates using trypsin (e.g., 0.25% (w/v) trypsin and 0.53 mM EDTA solution). The detached cells are then collected by centrifugation. The collected cells are re-suspended in fresh culture medium at an appropriate high density, such as the range of about $1 \times 10^5$ cells/ml to about $1 \times 10^6$ cells/ml. In this example, the cell density chosen was about $5 \times 10^5$ cells/ml. The preparation procedures are techniques known by the skilled artisan, such as, for example, procedures recommended by the ATCC. Obtaining the appropriate density is a matter of diluting or further concentrating the cells via additional acts of centrifugation and/or aspiration.

Using the cell stock suspension, C2C12 cells are seeded to form high-density spots on a support such as a tissue culture plate (e.g., a 100 mm Petri dish) that has been sterilized and treated (i.e., coated) with one or more extracellular matrix components and/or one or more adhesion proteins so as to provide a cell growth surface of attachment with uniform chemistry. An example of such a culture plate is the BD Falcon™ cell culture dish sold commercially by the vendor BD Biosciences. The spotting should be performed using aseptic techniques, For each spot, about 50 µl of cells are dispensed and transferred to the plate. Typically, this volume may form a spot having a diameter of about 1 to about 1.5 cm in the 100 mm dish. More than one high-density spot may be dispensed and positioned within the dish, with sufficient spacing from one another so as to permit growth along each spot's periphery without immediate contact to another high-density spot. For example, about 4 to about 6 spots in total may be spaced apart from one another in a 100 mm Petri dish. The manner of roughly even spacing of each spot of high-density seeding from one another is exemplified in FIG. 1.

The C2C12 cells are then allowed to initially or partially attach to the interior cell growth surface within the dish by incubating the plurality of cells at 37° C. for 1-2 hours. Afterwards, the unattached cells are washed off by gently adding 10 ml of 37° C. culture medium to one side of the Petri dish, followed by swirling of the dish. Care should be taken to avoid adding media directly onto the one or more spots, which has the potential of washing semi-attached cells off from the center of the one or more spots. The culture medium and unattached cells are then removed by aspiration.

Next, thirty (30) ml of proliferation (i.e., growth) medium are added to the Petri dish, and the dish is covered and incubated at 37° C. After 3 days of incubation, myotubes start to appear. A tissue model having a differentiation "time-line" can be seen at this time. Proliferating cells are observed aligned at the periphery of the enlarged cell spots, and myotubes are observed extending from near the center of the cell spots toward the periphery of the cell spots, as represented in the drawing of FIG. 5.

During this period of incubation, the cells are monitored by visual inspection daily, but culture vessels are left largely undisturbed. Culture media may be aspirated and replaced as needed. Subsequent medium changes, if they occur, should be about 10 ml of medium for a 100 ml dish. This step of media aspiration and replacement was not necessary (nth wally) until or near Day 13 of incubation. One skilled in the art will readily acknowledge a circumstance in which the culture media should be changed. For example, a skilled artisan might recognize that the culture media should be replaced based on color changes in a substance known as phenol red that is added to the media. The phenol red serves as an indicator of nutrient depletion and of an increase in acidity of the medium. Fresh medium that has phenol red added is typically rose red in color, whereas spent medium approaches yellow. A change of medium was performed if the color became orange. The one or more spots continued to grow in size outwardly and began to join other spots depending on the number of cell spots originally seeded and the original amount of distance between them.

By the thirteenth day of incubation, aligned, spontaneously contracting myotubes are observed. More myotubes with pronounced contractions are observed where two cell spots meet and join. The cells are maintained for an additional two weeks by daily replacement of fresh culture media. Many mature myotubes are observed to exhibit synchronized spontaneous contraction.

The above described example is an exemplary embodiment illustrating the manner and process of how to seed a high-density spot of a plurality of cells, how to allow the cells to proliferate from the periphery of the spot, and how to allow the cells to align, fuse, and differentiate. Methods of the exemplary embodiments described herein are based on a well-established cellular mechanism, i.e., contact inhibition, which is common with most anchorage dependent cell types. A person of ordinary skill in the art would appreciate, after having the benefit of the detailed description contained herein, that the above procedures may also be used, with little or no modifications, for other human or animal cell types that are anchorage dependent, such as cardiac muscle cells, bone cells, and nerve cells. Methods in accordance with the embodiments described herein may also be applied to culturing stem cells or de-differentiated cells.

In accordance with another embodiment, a method for forming a three-dimensional tissue model is described. For this embodiment, each monolayer of tissue model that would be formed by the method of high-density spot seeding previously described above may be stacked upon another monolayer using a lamination process in which a layer of extracellular matrix component (e.g., collagen, laminin, fibronectin, elastin, etc.) is positioned in between the two monolayers of tissue model. The resulting laminated tissue model would be three-dimensional. Alternatively, in yet another embodiment, other types of different cell types may also be formed using the method of high-density spot seeding, and each monolayer of tissue model formed may be stacked upon the other type(s) of tissue model(s). For example, monolayer models of nerve tissue or blood vessel tissue may be incorporated onto monolayer models of muscle tissue to produce a model tissue system having interacting tissue models. The methods described herein may enable formation of small pieces of tissue to he engineered for use in clinical applications in the field of regenerative medicine.

The embodiments directed to methods may be utilized to form tissue models, another exemplary embodiment, such as aligned, spontaneous contracting myotubes without the use of special medium, or without (costly, time-consuming) specialized substrates to induce cell alignment. The methods describe simple, reproducible, and cost-effective ways for making two-dimensional or three-dimensional tissue models. Such tissue models may have biomedical and regenerative applications, including tissue patching or repair using transplantable tissues, such as bone, skeletal muscle, and cardiac muscle.

Moreover, when combined with other cell culturing techniques, such as gene silencing, knock-up/knock-down of genes/proteins, and dominant negative mutants, the tissue models and differentiation "time-lines" generated by the methods of the embodiments may serve as powerful tools to elucidate the underlying mechanisms of cell differentiation, muscle atrophy, and molecular events associated with muscle contraction.

Although only a few exemplary embodiments of the invention have been described in detail above, those skilled in the art will readily appreciate that many modifications are possible in the exemplary embodiments without materially departing from the novel teachings and advantages of this invention. Accordingly, all such modifications are intended to he included within the scope of this invention as defined in the following claims. In the claims, means-plus-function and step-plus-function clauses are intended to cover the structures or acts described herein as performing the recited function and not only structural equivalents, but also equivalent structures. Thus, while a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. A method for making a model of aligned, contracting muscle tissue, comprising:
    seeding anchorage-dependent cells onto a support to form a cell spot, the cells having a range of concentration of from about $1\times10^5$ to about $1\times10^6$ cells per milliliter of culture medium, with the volume of each spot being within a range of about 20 µl to about 50 µl;
    incubating the cells for an initial period of time to allow the cells to partially attach to the support;
    removing any cells that have not partially attached to the support after the initial period of time of incubation;
    adding growth culture medium to the support after removing the unattached cells such that the partially attached cells proliferate about a periphery of the cell spot and differentiate away from the center of the cell spot, wherein the amount of growth culture medium added is a volume sufficient to enable the partially attached cells to proliferate undisturbed and without culture medium refresh for a period of time of at least seven days; and
    further incubating the cells to form the model of muscle tissue.

2. The method of claim 1, wherein the selected concentration is about $5\times10^5$ cells per milliliter of culture medium.

3. The method of claim 1, wherein the model of muscle tissue made is skeletal muscle tissue.

4. The method of claim 1, wherein the model of tissue made is a cardiac muscle tissue.

5. The method of claim 1, wherein the support is a plastic cell culture plate.

6. The method of claim 5, wherein the cell culture plate is coated with an extracellular matrix component and/or an adhesion protein to which the seeded cells attach, wherein the extracellular matrix component is selected from collagen, laminin, fibronectin, elastin, keratin, heparin sulfate, chondroitin sulfate, keratin sulfate, or hyaluronic acid, and wherein the adhesion protein is selected from an integrin or a cadherin.

7. The method of claim 1, wherein the cells are C2C12 cells or cells of a subclone of a C2 cell line, H9c2(2-1) cells, L6 cells, L8 cells, QM7 cells, So18 cells, G-7 cells, G-8 cells, other myoblast cells, stem cells, or dedifferentiated cells.

8. The method of claim 1, wherein the cells are C2C12 cells.

9. The method of claim 1, further comprising the steps of making a second layer of muscle tissue, made in the same manner as the first layer of muscle tissue made by the method of claim 1, positioning the second layer of muscle tissue on top of the first layer of muscle tissue, and positioning a layer of extracellular matrix component in between the first layer and the second layer of muscle tissue to generate a three-dimensional tissue model.

\* \* \* \* \*